(12) United States Patent
Ojima et al.

(10) Patent No.: US 10,550,093 B2
(45) Date of Patent: Feb. 4, 2020

(54) THIRD GENERATION TAXOIDS AND METHODS OF USING SAME

(71) Applicant: The Research Foundation for the State University of New York, Albany, NY (US)

(72) Inventors: Iwao Ojima, Port Jefferson, NY (US); Changwei Wang, Port Jefferson Station, NY (US); Xin Wang, Centereach, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/740,859

(22) PCT Filed: Jul. 1, 2016

(86) PCT No.: PCT/US2016/040615
§ 371 (c)(1),
(2) Date: Dec. 29, 2017

(87) PCT Pub. No.: WO2017/004478
PCT Pub. Date: Jan. 5, 2017

(65) Prior Publication Data
US 2018/0194744 A1   Jul. 12, 2018

Related U.S. Application Data

(60) Provisional application No. 62/187,510, filed on Jul. 1, 2015.

(51) Int. Cl.
*C07D 305/14* (2006.01)
*A61P 35/00* (2006.01)

(52) U.S. Cl.
CPC ............ *C07D 305/14* (2013.01); *A61P 35/00* (2018.01)

(58) Field of Classification Search
CPC .................................................. C07D 305/14
USPC ......................................... 549/511; 514/449
See application file for complete search history.

(56) References Cited

U.S. PATENT DOCUMENTS

| 6,096,909 | A | 8/2000 | Ojima | |
|---|---|---|---|---|
| 6,100,411 | A | 8/2000 | Ojima | |
| 6,458,976 | B1 | 10/2002 | Ojima | |
| 6,500,858 | B2 | 12/2002 | Ojima | |
| 7,981,926 | B2 * | 7/2011 | Ojima | C07D 305/14 514/449 |
| 2009/0118355 | A1 | 5/2009 | Ojima | |

FOREIGN PATENT DOCUMENTS

WO          9420484 A1     9/1994

OTHER PUBLICATIONS

Golub et al., Science, vol. 286, 531-537 (Year: 1999).*
Pearce et al., Failure modes in anticancer drug discovery and development, Cancer Drug Design and Discovery Edited by Stephen Neidle, Chapter 18, pp. 424-435 (Year: 2008).*
Simone, Oncology Introduction, Cecil Textbook of Medicine, ed. Bennett et al. W.B. Saunders CO. 20th ed., vol. 1, 1004-1010. (Year: 1996).*
Gura, Systems for identifying New Drugs Are Often Faulty, Cancer Models, Science, vol. 276, No. 5340, pp. 1041-1042. (Year: 1997).*
Johnson et al. Relationships between drug activity in NCI preclinical in vitro and in vivo models and early clinical trials, British Journal of Cancer 64(10): 1424-1431. (Year: 2001).*
Purser et al., "Fluorine in Medicinal Chemistry," Chem. Soc. Rev., vol. 37, pp. 320-330; 2008.
Seitz et al., "Design, Synthesis and Application of Fluorine-Labeled Taxoids as 19F NMR Probes for the Metabolic Stability Assessment of Tumor-Targeted Drug Delivery Systems," J. Fluor. Chem., vol. 171, pp. 148-161; 2015.
Ojima et al., "Design, Synthesis and Biological Evaluation of New Generation Taxoids," J. Med. Chem., vol. 51, No. 11, pp. 3203-3221; 2008.
Georg et al., "Taxane Anticancer Agents: Basic Science and Current Status," ACS Symp. Series 583, American Chemical Society, pp. 4131-4133;1995.

(Continued)

*Primary Examiner* — Patricia L Morris
(74) *Attorney, Agent, or Firm* — Hoffmann & Baron, LLP

(57) ABSTRACT

The invention includes taxoid compounds represented by the formula:

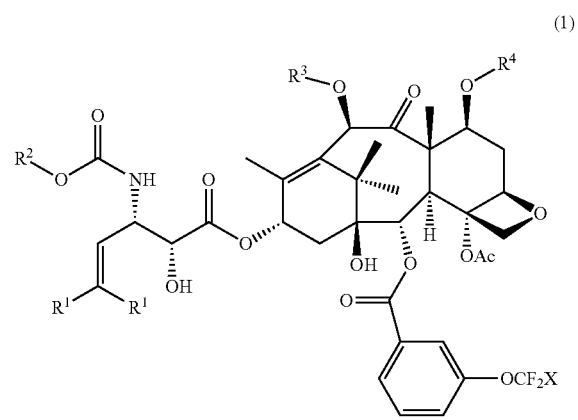

(1)

wherein: $R^1$ represents a methyl group or a fluorine; $R^2$ represents an alkyl or alkenyl group having one to six carbon atoms; or a cycloalkyl or cycloalkenyl group having three to seven ring carbon atoms; $R^3$ represents an alkyl, alkenyl, dialkylamino, alkylamino, or alkoxy group having one to six carbon atoms; a cycloalkyl or cycloalkenyl group having three to seven ring carbon atoms; an aryl group having six to eighteen ring carbon atoms; or a heteroaryl group having three to seventeen ring carbon atoms; $R^4$ represents hydrogen or a methyl group; and X represents hydrogen or fluorine.

10 Claims, 1 Drawing Sheet

(56) References Cited

OTHER PUBLICATIONS

Kuznetsova et al., "Syntheses and Biological Evaluation of Novel 3'-Difluorovinyl Taxoids", J. Fluor. Chem, vol. 143, pp. 177-188; 2012.

Kuznetsova et al., "Syntheses and Structure—Activity Relationships of Novel 3'-Difluoromethyl and 3'-Trifluoromethyl-Taxoids", J. Fluor. Chem, vol. 129, No. 9, pp. 817-828; 2008.

Ojima et al, "Anticancer Agents: Fronteirs in Cancer Chemotherapy," ACS Symp. Series 796, American Chemical Society, Washington, D.C., 2001.

Ojima et al., "Syntheses and Structure—Activity Relationships of the Second-Generation Antitumor Taxoids: Exceptional Activity against Drug-Resistant Cancer Cells", J. Med. Chem, vol. 39, pp. 3889-3896; 1996.

Ojima et al., "Synthesis and Structure-Activity Relationships of New Second-Generation Taxoids", Bioorganic & Medicinal Chemistry Letters, vol. 9, pp. 3423-3428; 1999.

Seitz, Joshua, et al, "Fluorine-containing taxoid anticancer agents and their tumor-targeted drug delivery", Journal of Fluorine Chemistry, Elsevier, vol. 152, May 24, 2013, pp. 157-165.

Supplementary European Search Report issued in European Patent Application No. EP 16818862 dated Dec. 10, 2018.

\* cited by examiner

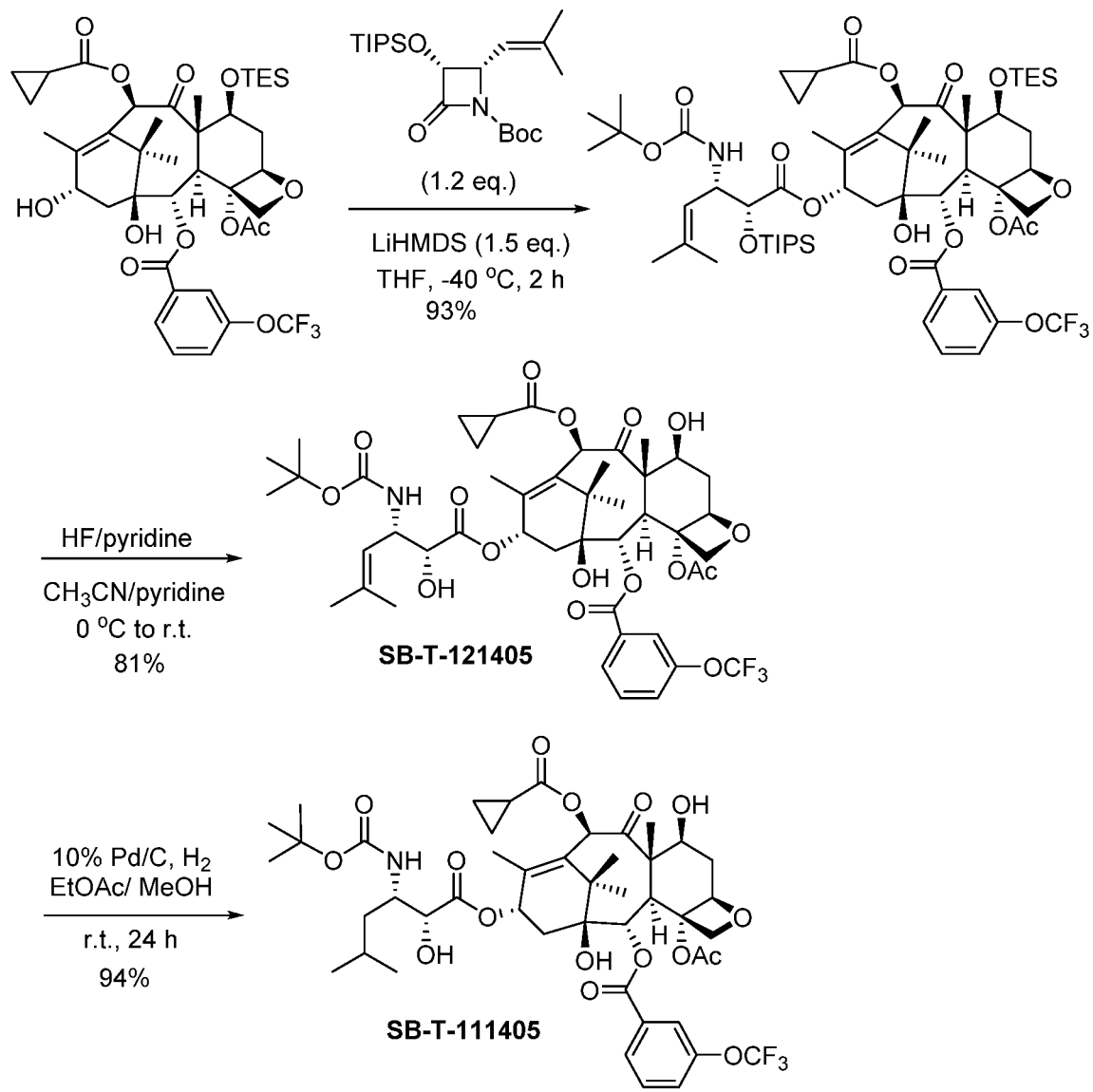

THIRD GENERATION TAXOIDS AND METHODS OF USING SAME

This application is the U.S. National Phase of International Patent Application No. PCT/US2016/040615, filed on Jul. 1, 2016, which claims the benefit of U.S. Provisional Application No. 62/187,510, filed on Jul. 1, 2015, the specifications of which are each incorporated by reference herein in their entireties for all purposes.

This invention was made with government support under grant numbers CA103314 awarded by the National Institute of Health. The government has certain rights in the invention.

BACKGROUND OF THE INVENTION

First generation taxoid compounds such as paclitaxel (Taxol®) and docetaxel (Taxotere®) have gained prominence as some of the most efficacious anticancer drugs. See E. K. Rowinsky, *Annual Review of Medicine* 1997, 48, 353; M. Suffness, *Taxol Science and Applications*; CRC Press: New York, 1995.

However, these first-generation taxane anticancer drugs exhibit little efficacy in treating melanoma, pancreatic, gastric, brain and renal cancers. These limitations are at least, in part, due to multi-drug resistance (MDR) caused by overexpression of ABC cassette efflux pumps and the beta-III tubulin isoform.

Second generation taxoid compounds with orders of magnitude higher potency have also been developed. See U.S. Pat. Nos. 6,096,909, 6,100,411, 6,458,976, and 6,500,858 to I. Ojima; G. I. Georg, T. Chen, I. Ojima, and D. M. Vyas (Eds.), "Taxane Anticancer Agents: Basic Science and Current Status," ACS Symp. Series 583; American Chemical Society, Washington, D.C., 1995); I. Ojima, et al, *Bioorg. Med. Chem. Lett.*, 1999, 9, 3423-3428; I. Ojima, et al, *J. Med. Chem.*, 1996, 39, 3889-3896; and I. Ojima, G. D. Vite, K.-H. Altmann (Eds.), "Anticancer Agents: Frontiers in Cancer Chemotherapy," ACS Symp. Series 796, American Chemical Society, Washington, D.C., 2001.

While these and other second generation taxoids have shown a high degree of efficacy in the treatment of various forms of cancer, there is a continuing need for improving the activity and mode of action of these compounds. There is a particular need to improve the efficacy of taxoid compounds against multi-drug resistance (MDR) in the treatment of cancer. There is also a need for taxoid compounds having less acute side effects and higher metabolic stability.

SUMMARY OF THE INVENTION

It has been surprisingly found that the incorporation of a trifluoromethoxy ($CF_3O$) or difluoromethoxy ($CF_2HO$) group at the C-2 benzoate moiety of second-generation taxoids increases the potency substantially; whereas, the introduction of a trifluoromethyl group decreases the potency. In particular, the "third generation" taxoids of this invention possess exceptionally high potency against drug-resistant cancer cell lines, superior to the "second-generation" taxoids. The $CF_3O$ or $CF_2HO$-incorporation was strategically designed to increase potency, block known metabolic pathways of taxoids by cytochrome P-450 class enzymes, and enhance drug transportation and membrane permeability.

Based on these surprising findings, a series of highly potent third-generation taxoids, bearing a m-OCF3 group at the C2-benzoate position, have been designed and synthesized using the beta-lactam synthon method. The potency of these third-generation taxoids was evaluated against various drug-sensitive and drug-resistant cancer cell lines, including MCF-7, NCI/ADR, ID-8, MX-1, PANC-1, CFPAC-1, HT-29, DLD-1, HCT-116, and patient-derived cancer stem cells, PC3-MM2, PPT2 and CR4. These taxoids can serve as chemotherapeutic agents with appropriate formulations and through conjugation to tumor-targeting molecules.

In one aspect of the invention, a taxoid compound is provided, represented by the formula:

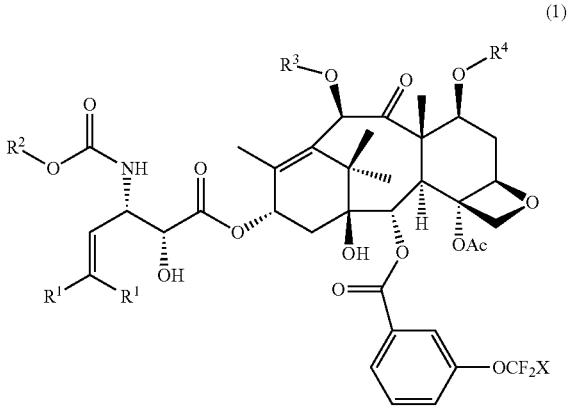

(1)

wherein:
$R^1$ represents a methyl group or a fluorine;
$R^2$ represents an alkyl or alkenyl group having one to six carbon atoms; or a cycloalkyl or cycloalkenyl group having three to seven ring carbon atoms;
$R^3$ represents an alkyl, alkenyl, dialkylamino, alkylamino, or alkoxy group having one to six carbon atoms; a cycloalkyl or cycloalkenyl group having three to seven ring carbon atoms; an aryl group having six to eighteen ring carbon atoms; or a heteroaryl group having three to seventeen ring carbon atoms;
$R^4$ represents hydrogen or a methyl group; and
X represents hydrogen or fluorine.

In some embodiments, $R^2$ represents tert-butyl.
In some embodiments, $R^1$ represents methyl, $R^2$ represents tert-butyl.
In some embodiments, $R^1$ represents fluorine, $R^2$ represents tert-butyl.
In some embodiments, $R^1$ represents methyl, $R^2$ represents tert-butyl, and X represents fluorine.
In some embodiments, $R^1$ represents fluorine, $R^2$ represents tert-butyl, and X represents fluorine.
In some embodiments, $R^1$ represents methyl, $R^2$ represents tert-butyl, and X represents hydrogen.
In some embodiments, $R^1$ represents fluorine, $R^2$ represents tert-butyl, and X represents hydrogen.
In some embodiments, $R^2$ represents tert-butyl, R3 presents acetyl, propanoyl, cyclopropanecarbonyl, N,N-dimethylcarbamoyl, and methoxycarbonyl.

In one aspect of the invention, a pharmaceutical composition comprising an aforementioned taxoid compound and a pharmaceutically acceptable carrier is provided.

In one aspect of the invention, a method for inhibiting the growth of cancer cells in a mammal in need thereof is provided. The method comprises administering to the mammal an effective amount of a taxoid compound according to the instant invention.

BRIEF DESCRIPTION OF FIGURES

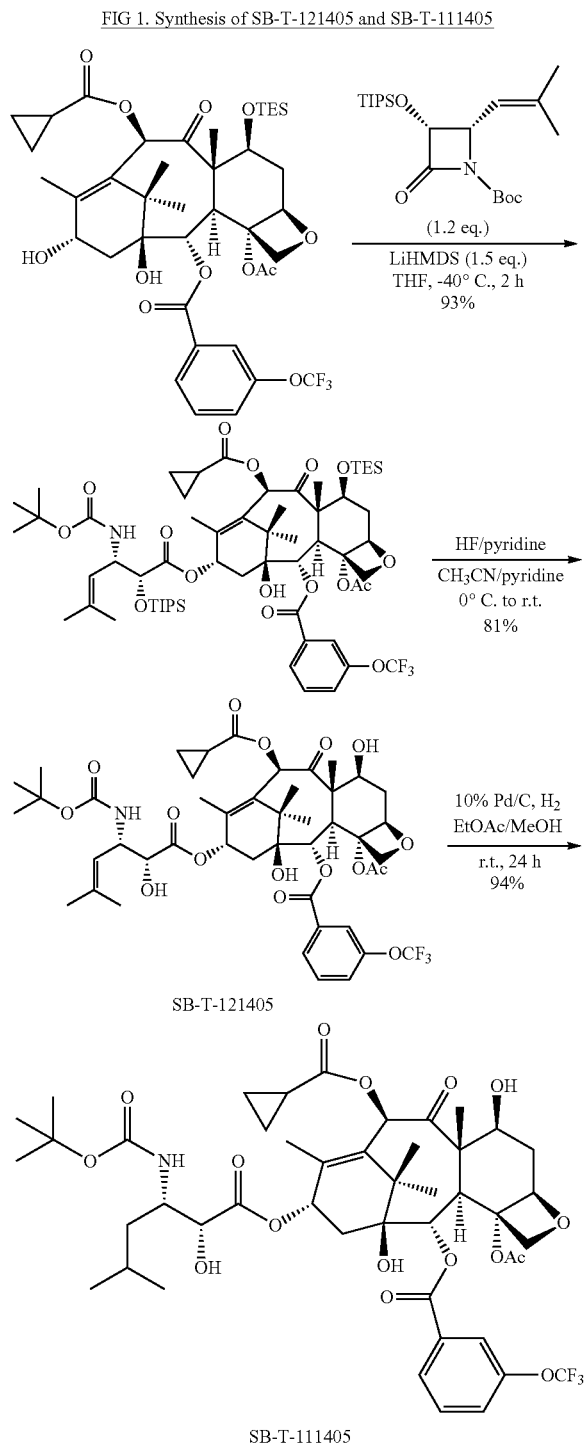

FIG 1. Synthesis of SB-T-121405 and SB-T-111405

DETAILED DESCRIPTION OF THE INVENTION

In one aspect, the invention relates to third generation taxoid compounds. These taxoid compounds contain a trifluoromethoxy ($CF_3O$) or difluoromethoxy ($CF_2HO$) group at the C-2 benzoate moiety, and do not contain a trifluoromethyl group at the C3' position.

The taxoids of this invention possess exceptionally high potency against drug-resistant cancer cell lines, superior to other series of the "second-generation" taxoids. The $CF_3O$ or $CF_2HO$-incorporation was strategically designed to increase potency, block known metabolic pathways of taxoids by cytochrome P-450 class enzymes, and enhance drug transportation and membrane permeability. These "third-generation" taxoids possess exceptionally high potency against drug-resistant cancer cell lines, superior to paclitaxel, docetaxel and cabazitaxel as well as to the "second-generation" taxoids.

In a preferred embodiment, the taxoid compounds of the invention are represented by the formula:

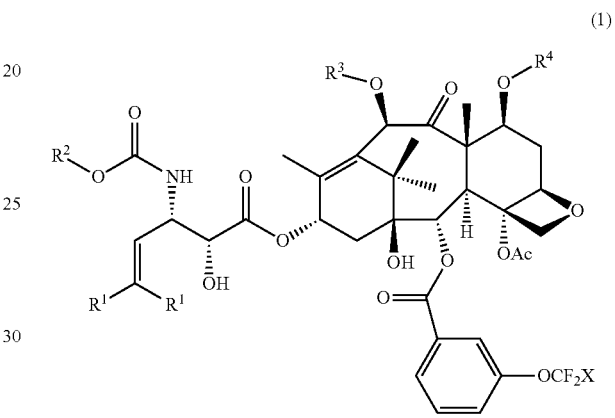

(1)

In formula (1), $R^1$ represents a methyl group or a fluorine; $R^2$ represents an alkyl or alkenyl group having one to six carbon atoms; or a cycloalkyl or cycloalkenyl group having three to seven ring carbon atoms; $R^3$ represents an alkyl, alkenyl, dialkylamino, alkylamino, or alkoxy group having one to six carbon atoms; a cycloalkyl or cycloalkenyl group having three to seven ring carbon atoms; an aryl group having six to eighteen ring carbon atoms; or a heteroaryl group having three to seventeen ring carbon atoms; $R^4$ represents hydrogen or a methyl group; and X represents hydrogen or fluorine.

Some examples of suitable straight-chained alkyl groups include methyl, ethyl, n-propyl, n-butyl, n-pentyl, and n-hexyl.

Some examples of suitable branched alkyl groups include iso-propyl, iso-butyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, and 4-methylpentyl.

Some examples of suitable straight-chained alkenyl groups include vinyl, 2-propen-1-yl, 2-buten-1-yl, 3-buten-1-yl, 2-penten-1-yl, 3-penten-1-yl, 1,3-pentadien-1-yl, 4-penten-1-yl, 2-hexen-1-yl, 3-hexenyl, 4-hexen-1-yl, and 5-hexen-1-yl.

Some examples of suitable branched alkenyl groups include propen-2-yl, 1-buten-2-yl, 2-buten-2-yl, 1-buten-3-yl, 1-penten-2-yl, 1-penten-3-yl, 1-penten-4-yl, 2-penten-2-yl, 2-penten-3-yl, 2-penten-4-yl, 1-buten-3-methyl-2-yl, 1-buten-3-methyl-3-yl, 2-buten-2-methyl-1-yl, 2-buten-2-methyl-3-yl, 2-buten-2-methyl-4-yl, 2-buten-2-methylenyl, 2-buten-2,3-dimethyl-1-yl, 1-hexen-2-yl, 1-hexen-3-yl, 1-hexen-4-yl, 1-hexen-5-yl, 2-hexen-3-yl, 2-hexen-4-yl, 2-hexen-5-yl, 3-hexen-2-yl, 3-hexen-3-yl, 1-penten-3-methyl-2-yl, 1-penten-3-methyl-3-yl, 1-penten-3-methyl-4-yl, 2-penten-3-methyl-2-yl, and 2-penten-3-methyl-4-yl.

Some examples of suitable alkylamino groups include methylamino, ethylamino, n-propylamino, iso-propylamino, n-butylamino, sec-butylamino, iso-butylamino, tert-butylamino, n-pentylamino, iso-pentylamino, neo-pentylamino, n-hexylamino, 2,3-dimethylbutylamino, cyclopropylamino, cyclobutylamino, cyclopentylamino, cyclohexylamino, cycloheptylamino, 2-hydroxyethylamino, 2-(2-hydroxyethyleneoxy)-ethylamino, 2-methoxyethylamino, 2-ethoxyethylamino, and 3-hydroxypropylamino.

Some examples of suitable dialkylamino groups include dimethylamino, methylethylamino, methyl(n-propyl)amino, methyl(iso-propylamino), methyl(n-butyl)amino, methyl(iso-butyl)amino, methyl(n-pentyl)amino, methyl(iso-pentyl)amino, methyl(neopentyl)amino, diethylamino, ethyl(n-propyl)amino, ethyl(iso-propylamino), ethyl(n-butyl)amino, ethyl(iso-butyl)amino, di(n-propyl)amino, and di(iso-propyl)amino.

Some examples of suitable alkoxy groups include methoxy, ethoxy, n-propoxy, iso-propoxy, n-butoxy, iso-butoxy, sec-butoxy, tert-butoxy, n-pentoxy, 1-methylbutoxy, 2-methylbutoxy, 3-methylbutoxy, n-hexoxy, 1,1-dimethylbutoxy, 1,2-dimethylbutoxy, 2,2-dimethylbutoxy, 2,3-dimethylbutoxy, 1-ethylbutoxy, 2-ethylbutoxy, cyclopropyloxy, cyclobutyloxy, 2,4-dimethylcyclobutyloxy, cyclohexyloxy, cyclopropylmethyloxy, cyclohexylmethyloxy, and phenoxy.

The non-aromatic cycloalkyl or cycloalkenyl groups have three to seven ring carbon atoms. Some examples of suitable cyclic alkyl groups include cyclopropyl, cyclobutyl, cyclopentyl, cyclohexyl, and cycloheptyl. Some examples of suitable cyclic alkenyl groups include cyclobutenyl, cyclobutadienyl, cyclopentenyl, cyclohexenyl, cyclohexadienyl, cycloheptenyl, and cycloheptadienyl.

The non-aromatic cycloalkyl or cycloalkenyl groups can also be a non-aromatic heterocyclic group. Some examples of suitable non-aromatic heterocyclic groups include piperidinyl, piperidinyl-N-oxide, N-methylpiperidinyl, piperazinyl, 1-methylpiperazinyl, piperazinyl-N-oxide, 1-acetylpiperazinyl, 1-(o-tolyl)piperazinyl, homopiperazinyl, and morpholino.

The cyclic groups described above can be fused or unfused. The total number of carbon atoms include carbon atoms from fused rings.

Suitable aryl groups have six to eighteen carbon atoms. A preferred unfused carbocyclic aryl group is phenyl. Some examples of suitable fused aryl groups include naphthyl, phenanthryl, anthracenyl, triphenylenyl, chrysenyl, and pyrenyl.

Suitable heterocyclic aryl groups have three to seventeen atoms in the ring with one or more heteroatoms, preferably nitrogen, sulfur, or oxygen atoms. Some examples of suitable heteroaryl groups include pyridinyl, pyrimidinyl, triazinyl, imidazolyl, benzimidazolyl, pyrrolyl, cinnolinyl, phthalazinyl, quinazolinyl, purinyl, 2,6-naphthyridinyl, 1,8-naphthyridinyl, quinolinyl, isoquinolinyl, carbazolyl, oxazolyl, thiophenyl, thiazolyl, furyl, pyridazinyl, pyrazolyl, 1,4-diazanaphthalenyl, indolyl, pyrazinyl, 4,5-diazaphenanthrene, and benzoxazole.

The cycloalkyl, cycloalkenyl, aryl, heteroaryl and non-aromatic heterocyclic rings described above can be substituted with any of the hydrocarbon groups thus far described.

Some examples of hydrocarbyl-substituted cycloalkyl groups include 2-methylcyclopropyl, 2-ethylcyclopropyl, 2-methylcyclobutyl, 3-methylcyclobutyl, 2-methylcyclopentyl, 2,3-dimethylcyclopentyl, 3-iso-propylcyclopentyl, 2,6-dimethylcyclohexyl, 4-(t-butyl)cyclohexyl, 2-vinylcyclohexyl, 3-allylcyclopentyl, 3,4-diallylcyclopentyl, 1-(4-pyridinyl)piperidinyl, 1-(4-pyridinylmethyl)piperidinyl, 4-(4-pyridinyl)piperidinyl, 4-(4-pyridinyl)piperazin-1-yl, and bicyclohexyl groups.

Some examples of hydrocarbyl-substituted cycloalkenyl groups include 3-methyl-3-cyclopenten-1-yl, 3,4-dimethyl-3-cyclopenten-1-yl, 2-iso-propyl-2-cyclopenten-1-yl, 2,3-diethyl-2-cyclopenten-1-yl, 4-vinyl-1-cyclohexen-1-yl, 3,4-diethyl-3-cyclopenten-1-yl, and 3,4-diallyl-3-cyclopenten-1-yl groups.

Some examples of hydrocarbyl-substituted aryl groups include tolyl, mesityl, xylyl, cumenyl, cymenyl, 3,5-di(t-butyl)phenyl, 2-methylnaphthyl, 2-vinylphenyl, 2-vinylbenzyl, 2-vinylnaphthyl, 4-cyclohexylphenyl, biphenyl, 4-(4-piperidinyl)pyridinyl, and p-terphenyl groups.

Some examples of hydrocarbyl-substituted heteroaryl groups include 2-methylpyridin-1-yl, 2-ethylpyridin-1-yl, 3-vinylimidazol-1-yl, 2-methylimidazol-1-yl, 2-methylquinoxalin-1-yl, 1-allylbenzotriazolyl, 2,2'-bipyridyl, 4,4'-bipyridyl, 4-methylpyrazinyl, 4-(pyridinylmethyl)-pyridinyl, 4-benzylpyrazinyl, nicotinamidyl, 2-methylfuranyl, 5-methylfurfurylamino, 2-methylthiopheneyl, 4-methyloxazolyl, 2,5-diphenyl-4-methyloxazolyl, and 4-methylthiazolyl groups.

Alternatively, the cycloalkyl, cycloalkenyl, aryl, heteroaryl and non-aromatic heterocyclic rings described above can be substituted with a halogen, nitro, hydroxyl carboxyl, amino or azido group.

Some particularly preferred taxoid compounds of the present invention include those listed in the table below. These taxoids have shown particular potency for the inhibition of the growth of cancer cells as shown in the following table.

Cytotoxicity of Third-Generation Taxoids ($IC_{50}$ nM)

|  | MCF7 | NCI/ADR | LCC6-WT | LCC6-MDR | ID8 | CFPAC-1 | PANC-1 |
| --- | --- | --- | --- | --- | --- | --- | --- |
| paclitaxel | 3.13 | 361 | 3.10 | 346 | 2.02 | 68 | 3.78 |
| SB-T-121205 | 0.23 | 3.6 | 0.45 | 4.06 | 0.23 | 0.40 | 0.76 |
| SB-T-121305 | 1.74 | 6.5 | 1.54 | 4.96 |  | 1.75 | 1.12 |
| SB-T-121405 | 0.98 | 3.3 | 1.01 | 4.63 | 0.33 | 0.36 | 0.32 |
| SB-T-121605 |  |  |  |  | 0.25 | 0.56 | 0.54 |
| SB-T-121705 | 0.98 | 6.1 | 0.59 | 2.40 |  | 0.8 | 1.17 |
| SB-T-111405 |  |  |  | 0.98 | 0.28 | 2.3 | 0.56 |

-continued

|  | MCF7 | NCI/ ADR | LCC6-WT | LCC6-MDR | ID8 | CFPAC-1 | PANC-1 |
|---|---|---|---|---|---|---|---|
| SB-T-111605 |  |  |  | 7.93 | 1.43 | 2.9 | 0.62 |
| SB-T-123005 | 2.46 | 45.6 |  | 16.9 | 1.43 | 7.3 | 0.87 |
| SB-T-1230105 |  |  | 0.55 | 6.98 |  |  | 0.98 |
| SB-T-121206 | 0.31 | 4.2 | 0.28 | 1.45 | 0.35 | 0.23 | 0.49 |
| SB-T-121306 | 0.54 | 1.8 | 0.81 | 1.91 |  | 0.17 | 0.49 |
| SB-T-121406 | 0.29 | 2.2 | 0.33 | 2.03 |  | 0.31 | 0.75 |
| SB-T-121706 | 0.12 | 4.4 | 0.46 | 2.73 |  | 0.15 | 1.06 |
| SB-T-1230106 |  |  | 0.72 | 4.70 |  |  |  |

MCF7 and MX-1: human breast cancer cell lines.
LCC6-MDR: drug resistant (Pgp+) human breast cancer cell line.
NCI/ADR: drug resistant (Pgp+) human ovarian cancer cell line.
ID8: murine ovarian cancer cell line.
DLD-1 and HCT116: human colon cancer cell lines.
PANC-1 and CFPAC-1: human pancreatic cancer cell lines.

The taxoid compounds are either uncharged or in the form of pharmaceutically acceptable salts. The term "pharmaceutically acceptable salt" refers to a salt prepared from a suitable compound and, for example, an acid or a base. The salt is acceptably non-toxic and has acceptable pharmacokinetics. Such salts are formed by procedures known in the art.

Suitable acids for producing salts of the compounds of the invention include mineral acids and organic acids. Some examples of mineral acids include hydrochloric, hydriodic, hydrobromic, phosphoric, metaphosphoric, nitric and sulfuric acids. Some examples of organic acids include tartaric, acetic, citric, maleic, malic, benzoic, glycollic, gluconic, gulonic, succinic, arenesulfonic, e.g. p-toluenesulfonic acids, and the like.

Suitable bases for producing salts of the compounds of the invention include inorganic bases and organic bases. Some examples of inorganic bases include ammonia and the hydroxides of lithium, sodium, potassium, magnesium and calcium. Some examples of organic bases include primary, secondary, and tertiary alkyl amines.

In another aspect, the invention is directed to a pharmaceutical composition comprising a compound according to formula (1) and a pharmaceutically acceptable carrier. Compositions can, for example, be pills, capsules, solutions, creams, etc.

In this specification, a pharmaceutically acceptable carrier is considered to be synonymous with a vehicle or an excipient as understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical formulation may also include one or more of the following: a stabilizer, a surfactant, preferably a nonionic surfactant, and optionally a salt and/or a buffering agent.

The stabilizer can be, for example, an amino acid, e.g., glycine; or an oligosaccharide, e.g., sucrose, tetralose, lactose or a dextran. Alternatively, the stabilizer may be a sugar alcohol, e.g., mannitol; or a combination thereof.

The surfactant may be, for example, an ionic surfactant, such as a polyacrylate. Alternatively, the surfactant may be a nonionic surfactant, such as a polyethylene glycol, polyoxyethylene polyoxypropylene glycol, or polysorbate. Some examples of such nonionic surfactants include Tween 20, Tween 80, and Pluronic F-68 at from about 0.001% (w/v) to about 10% (w/v).

The salt or buffering agent may be any salt or buffering agent, such as, for example, sodium chloride, sodium or potassium phosphates, citric acid, sodium or potassium citrates, or a mixture thereof. The buffering agent is useful for maintaining the pH of the compounds of the invention. The salt and/or buffering agent is also useful to maintain the osmolality at a level suitable for administration to a mammal. For example, the salt or buffering agent can be present at a roughly isotonic concentration of about 150 mM to about 300 mM.

The pharmaceutical compositions of the inventions may additionally contain one or more conventional additives. Some examples of such additives include a solubilizer, such as, for example, glycerol; an antioxidant such as, for example, benzalkonium chloride (a mixture of quaternary ammonium compounds, known as "quat"), benzyl alcohol, chloretone or chlorobutanol; an anaesthetic agent such as, for example, a morphine derivative; or an isotonic agent, etc. As a further precaution against oxidation or other spoilage, the compounds of the inventions may be stored under nitrogen gas in vials sealed with impermeable stoppers.

When aqueous suspensions are used for oral administration, emulsifying and/or suspending agents are commonly added. In addition, coloring, sweetening and/or flavoring agents may be added to the oral compositions.

Pharmaceutical compositions are preferably sterile. The pH of the solutions can be suitably adjusted and buffered. For intravenous use, the total concentration of the solute(s) can be controlled in order to render the preparation isotonic.

Carrier compositions deemed to be suited for topical use include gels, salves, lotions, creams, ointments and the like. The compounds can also be incorporated with a support base or matrix or the like which can be directly applied to skin.

In another aspect, the invention is directed to inhibiting the growth of cancer cells in a mammal in need thereof. In the method, an effective amount of a compound of the invention is administered to a mammal.

The cancer cells can be any type of cancer treatable by the taxoid compounds. For example, the cancer can be breast, ovary, lung, head, neck, colon, pancreatic, melanoma, brain, prostate, or renal cancer.

Any mammal in need thereof can be treated in accordance with the present invention. Mammals include, for example, humans, baboons, and other primates, as well as pet animals such as dogs and cats, laboratory animals such as rats and mice, and farm animals such as horses, sheep, and cows.

The method of the invention comprises administering an effective amount of an instant taxoid. An effective amount of an instant taxoid is any amount effective in treating cancer or for inhibiting the growth of cancer cells in a mammal in need thereof.

The actual administered amount of the instant taxoid compound will vary according to various factors well known in the art, e.g., the type of cancer, the particular taxoid being administered, the mode of administration, and the particular subject being treated. The amount required for effective treatment is governed by pharmacological standards and by the discretion of medical practitioners in the art. For example, the effective amount can be determined during clinical and pre-clinical trials by methods familiar to physicians and clinicians.

The minimum amount of a taxoid administered to a human is the lowest amount capable of inhibiting the growth of cancer cells. The maximum amount is the highest effective amount that does not cause undesirable or intolerable side effects. The minimum amount can be, for example, 0.01, 0.05, or 0.1 milligrams per kilogram body weight per day. The maximum amount can be, for example, 10, 50, or 100 milligrams per kilogram body weight per day. Higher doses may be employed to treat the cancer to the extent patient tolerance permits.

The taxoid formulation may be administered alone or as an adjunct with other conventional drugs for treating cancer. The adjunctive drugs can be, for example, chemotherapy drugs. Some examples of chemotherapy drugs include methotrexate (Abitrexate®), fluorouracil (Adrucil®), hydroxyurea (Hydrea®), and mercaptopurine (Purinethol®).

The taxoid formulation may be administered by any suitable method known in the art. Some examples of suitable modes of administration include oral, systemic, and topical administration.

For oral administration, liquid or solid oral formulations can be used, as known in the art. Some examples of formulations suitable for oral administration include tablets, capsules, pills, troches, elixirs, suspensions, and syrups.

Systemic administration includes enteral or parenteral modes of administration, e.g., intravenous; intramuscular; subcutaneous; or intraperitoneal modes of administration. For example, the taxoid formulation may be administered by injection of a solution or suspension; or intranasally, in the form of, for example, a nebulizer, liquid mist, or intranasal spray; or transdermally, in the form of, for example, a patch; or rectally, in the form of, for example, a suppository; or intrabronchially, in the form of, for example, an inhaler spray.

Suitable carrier compositions for topical use include gels, salves, lotions, creams, ointments, and the like. The compounds can also be incorporated with a support base or matrix or the like which can be directly applied to skin.

The timing of the administration of the taxoid formulation may also be modified. For example, the formulation may be administered intermittently or by controlled release. Controlled release administration is a method of drug delivery to achieve a certain level of the drug over a particular period of time. See, for example, U.S. Patent Publication No. 2004/0115261, incorporated herein by reference.

EXAMPLES

Examples have been set forth below for the purposes of illustration and to describe the best mode of the invention at the present time. However, the scope of the invention is not to be in any way limited by the examples set forth herein.

Example 1

2-Debenzoyl-2-(3-trifluromethoxybenzoyl)-3'-dephenyl-10-(cyclopropanlcarbonyl)-3'-(2-methyl-2-propenyl)docetaxel (SB-T-121405)

2-Debenzoyl-2-(3-trifluromethoxybenzoyl)-7-triethylsilyl-10-deacetyl-10-cyclo-propanecarbonyl-baccatin [Ref 1] (122 mg, 0.151 mmol, 1 eq.) was dissolved in 8 mL dry tetrahydrofuran (THF) and cooled to −40° C. 1M lithium hexamethyldisilazide (LiHMDS) in THF (0.22 mL, 0.220 mmol, 1.5 eq.) and (3R,4S)-1-tert-butoxycarbonyl-3-triisopropyloxy-4-(2-methylprop-1-enyl)azetidin-2-one [Ref 2] (72 mg, 0.181 mmol, 1.2 eq.) were added into the mixture sequentially. The reaction was kept at −40° C. and monitored via thin-layer chromatography (TLC). Upon completion, the reaction was quenched by saturated ammonium chloride (5 mL), and the reaction mixture was extracted by ethyl acetate (3×5 mL), washed by saturated brine (5 mL), dried over anhydrous magnesium sulfate and concentrated in vacuo to give crude product. Further purification was made by column chromatography on silica gel (hexanes:ethyl acetate=3:1) to give 2-debenzoyl-2-(3-trifluromethoxybenzoyl)-7-triethylsilyl-2'-triisopropylsilyl-3'-dephenyl-10-(cyclopropanecarbonyl)-3'-(2-methyl-2-propenyl)docetaxel (159 mg, 93% yield) as a white solid: $^1$H NMR. $^1$H NMR (400 MHz, $CDCl_3$) δ 0.54-0.57 (m, 6H), 0.89-0.93 (m, 13H), 1.04-1.06 (m, 32H), 1.19-1.25 (m, 11H), 1.33 (s, 9H), 1.68 (s, 3H), 1.75 (d, J=5.6 Hz, 9H), 1.87 (dt, J=1.6 Hz, 11.4 Hz, 1H), 2.01 (d, J=11.4 Hz, 3H), 2.34 (s, 5H), 2.47-2.55 (m, 1H), 3.85 (d, J=7.2 Hz, 1H), 4.13 (dd, J=7.2 Hz, 14.4 Hz, 2H), 4.27 (d, J=8.0 Hz, 2H), 4.45 (dd, J=6.8 Hz, 12.4 Hz, 2H), 4.73-4.80 (m, 2H), 4.96 (t, J=8.8 Hz, 1H), 5.29 (t, J=8.8 Hz, 1H), 5.67 (d, J=7.2 Hz, 1H), 6.05 (t, J=8.8 Hz, 1H), 6.49 (s, 1H), 7.45 (d, J=8.4 Hz, 1H), 7.52 (t, J=8.4 Hz, 1H), 7.98 (s, 1H), 8.05 (d, J=8.4 Hz, 1H).

2-Debenzoyl-2-(3-trifluromethoxybenzoyl)-2'-triisopropylsilyl-7-triethylsilyl-10-(cyclopropanecarbonyl)-3'-dephenyl-3'-(2-methyl-2-propenyl)docetaxel (156 mg, 0.138 mmol, 1 eq.) was dissolved in 4 mL mixture of acetonitrile and pyridine (1:1) and cooled to 0° C. HF/pyridine 1.6 mL was added dropwise at 0° C. The reaction mixture was kept at −40° C. and the reaction was monitored via TLC. Upon completion, the reaction was quenched by 0.2 M citric acid (4 mL), and the reaction mixture was extracted by ethyl acetate (3×5 mL). The organic layer was washed by saturated copper sulfate (4 mL) and brine (4 mL), dried over anhydrous $MgSO_4$ and concentrated in vacuo to obtain crude product. Purification by column chromatography on silica gel (hexanes:ethyl acetate=1:1) gave 2-debenzoyl-2-(3-trifluromethoxybenzoyl)-10-(cyclopropanlcarbonyl)-3'-dephenyl-3'-(2-methyl-2-propenyl)docetaxel (SB-T-121405) (105 mg, 81% yield) as a white solid: $^1$H NMR (400 MHz, $CDCl_3$) δ 0.83-0.88 (m, 1H), 0.96-0.99 (m, 2H), 1.02-1.03 (m, 2H), 1.05 (s, 3H), 1.27 (s, 4H), 1.35 (s, 6H), 1.43 (s, 1H), 1.67 (s, 3H), 1.75 (d, J=12.0 Hz, 6H), 1.87 (dt, J=2.4 Hz, 11.6 Hz, 1H), 1.90 (s, 3H), 2.33 (s, 3H), 2.38 (t, J=8.4 Hz, 2H), 2.51-2.59 (m, 2H), 3.82 (d, J=7.2 Hz, 1H), 4.17 (t, J=8.4 Hz, 2H), 4.28 (d, J=8.4 Hz, 2H), 4.42 (dd, J=6.8 Hz, 1.2 Hz, 1H), 4.72 (s, 2H), 4.98 (d, J=8.4 Hz, 1H), 5.33 (d, J=5.6 Hz, 1H), 5.65 (d, J=7.2 Hz, 1H), 6.15 (t, J=9.2 Hz, 1H), 6.31 (s, 1H), 7.46 (d, J=7.2 Hz, 1H), 7.54 (t, J=8.0 Hz, 1H), 7.99 (s, 1H), 8.05 (d, J=8.0 Hz, 1H); $^{13}$C NMR (100 MHz, CDCl$_3$) δ 9.52, 13.23, 15.21, 18.60, 22.24, 25.87, 26.99, 28.40, 35.64, 43.37, 45.86, 51.80, 58.75, 72.53, 73.84, 75.73, 76.51, 79.41, 80.11, 81.23, 84.68, 120.74, 122.36, 126.36, 128.86, 130.52, 131.50, 132.95, 138.27, 143.12, 149.47, 155.59, 165.67, 170.21, 173.48, 175.34, 204.07; $^{19}$F NMR (376 MHz, CDCl$_3$) δ −57.83 (s, 3F); HRMS (TOF) m/z: Calcd. For $C_{46}H_{58}F_3NO_{16}H^+$, 938.3780. Found, 938.3778.

Ref 1: J. D. Seitz, J. G. Vineberg, L. Wei, J. F. Khan, B. Lichtenthal, C.-F. Lin and I. Ojima' *J. Fluor. Chem.* 171, 148-161 (2015).

Ref 2: I. Ojima, J. C. Slater, S. D. Kuduk, C. S. Takeuchi, R. H. Gimi, C.-M. Sun, Y. H. Park, P. Pera, J. M. Veith, and R. J. Bernacki, *J. Med. Chem.* 40, 267-278 (1997).

Example 2

2-Debenzoyl-2-(3-trifluromethoxybenzoyl)-3'-dephenyl-10-(cyclopropanecarbonyl)-3'-(2-methylpropyl)docetaxel (SB-T-111405)

To a solution of SB-T-121405 (50 mg, 0.0578 mmo) in 25 mL ethyl acetate and 0.05 mL methanol was added 10% palladium on carbon (6 mg, 0.0058 mmol, 0.1 eq.) at room temperature. The mixture was stirred at room temperature for 24 hours. The progress of the reaction was monitored by mass spectroscopy. Upon completion, the reaction mixture was filtered through celite pad, and washed with ethyl acetate (3×5 mL). The combined solution was washed with saturated copper sulfate (4 mL) and brine (4 mL), dried over anhydrous magnesium sulfate and concentrated in vacuo to give crude product. Purification column chromatography on silica gel (hexanes:ethyl acetate=1:1) gave 2-debenzoyl-2-(3-trifluromethoxybenzoyl)-3'-dephenyl-10-(cyclopropanlcarbonyl)-3'-(2-methyl-2-propanyl)-docetaxel (SB-T-111405) (47 mg, 94% yield) as a white solid; $^1$H NMR (400 MHz, CDCl$_3$) δ 0.96-0.99 (m, 9H), 1.14 (s, 5H), 1.30 (s, 14H), 1.67 (s, 8H), 1.87 (m, 4H), 2.331 (s, 3H), 2.51-2.59 (m, 2H), 3.20 (s, 1H), 3.81 (d, J=7.0 Hz, 1H), 4.09 (s, 1H), 4.15 (t, J=8.0 Hz, 1H), 4.26 (d, J=8.5 Hz, 1H), 4.41 (s, 1H), 4.57 (d, J=8.5 Hz, 1H), 4.97 (d, J=9.0 Hz, 1H), 5.63 (d, J=7.0 Hz, 1H), 6.15 (t, J=8.5 Hz, 1H), 6.30 (s, 1H), 7.44 (d, J=7.5 Hz, 1H), 7.52 (t, J=9.0 Hz, 1H), 7.98 (s, 1H), 8.04 (d, J=7.5 Hz, 1H); $^{13}$C NMR (100 MHz, CDCl$_3$) δ 9.46, 13.03, 14.98, 21.99, 23.23, 24.66, 26.61, 28.15, 35.64, 41.21, 43.18, 45.62, 51.37, 58.52, 72.69, 79.18, 79.64, 81.03, 84.68, 119.39, 122.22, 126.14, 128.68, 130.31, 131.30, 132.75, 142.88, 149.27, 155.47, 165.49, 169.90, 174.08, 175.15, 203.87.

Example 3

Other third-generation taxoids bearing a 3-trifluoromethoxybenzoyl group at the C2 position were synthesized and characterized in a similar manner as described in Examples 1 and 2.

2-Debenzoyl-2-(3-trifluromethoxybenzoyl)-3'-dephenyl-10-acetyl-3'-(2-methyl-2-propenyl)docetaxel (SB-T-121205)

White solid; $^1$H-NMR (400 MHz, CDCl$_3$, ppm) δ 1.14 (s, 3H), 1.25 (s, 3H), 1.33 (s, 9H), 1.66 (s, 3H), 1.73 (s, 9H), 1.75 (s, 3H), 1.84-1.90 (m, 5H), 2.23 (s, 3H), 2.33-2.41 (m, 5H), 2.52-2.58 (m, 1H), 3.47 (bs, 1H), 3.82 (d, J=7.0 Hz, 1H), 4.09-4.19 (m, 2H), 4.26 (d, J=8.3 Hz, 1H), 4.41 (dd, J=10.7 Hz, 7.0 Hz, 1H), 4.70-4.75 (m, 1H), 4.85 (d, J=8.3 Hz, 1H), 4.97 (d, J=8.3 Hz, 1H), 5.32 (d, J=8.3 Hz, 1H), 5.64 (d, J=7.0 Hz, 1H), 6.13 (t, J=8.3 Hz, 1H), 6.31 (s, 1H), 7.44 (d, J=8.0 Hz, 1H), 7.51 (t, J=8.0 Hz, 1H), 7.96 (s, 1H), 8.02 (d, J=8.0 Hz, 1H); $^{13}$C-NMR (100 MHz, CDCl$_3$) δ 9.66, 14.34, 15.12, 18.53, 21.00, 21.19, 21.94, 22.32, 25.81, 26.74, 28.35, 35.59, 35.73, 43.32, 45.87, 51.76, 58.64, 60.58, 72.27, 72.49, 73.80, 75.79, 75.85, 76.44, 77.43, 79.27, 79.98, 81.14, 84.59, 116.72, 119.29, 120.77, 121.86, 122.30, 124.43, 126.28, 128.81, 130.46, 131.48, 132.85, 138.06, 142.96, 149.38, 149.40, 155.55, 165.58, 170.20, 171.40, 173.41, 203.82; $^{19}$F NMR (376 MHz) δ −57.82 (s, 3F).

(a) 2-Debenzoyl-2-(3-trifluromethoxybenzoyl)-3'-dephenyl-10-propanoyl-3'-(2-methyl-2-propenyl)-docetaxel (SB-T-121305)

White solid; $^1$H NMR (500 MHz, CDCl$_3$) δ 1.15 (s, 3H), 1.24 (t, J=4.0 Hz, 4H), 1.33 (s, 9H), 1.68 (s, 4H), 1.72 (s, 4H), 1.75 (s, 3H), 1.87 (dt, J=3.0 Hz, 9.5 Hz, 1H), 1.93 (s, 3H), 2.03 (s, 1H), 2.33 (s, 4H), 2.38-2.43 (m, 1H), 2.49 (d, J=4.5 Hz, 1H), 2.53-2.59 (m, 1H), 3.37 (d, J=6.5 Hz, 1H), 3.79 (d, J=7.0 Hz, 1H), 3.86 (s, 3H), 4.09 (dd, J=8.5 Hz, 7.0 Hz, 1H), 4.17 (t, J=3.0 Hz, 2H), 4.27 (d, J=3.0 Hz, 1H), 4.40 (dt, J=4.5 Hz, 2.0 Hz, 1H), 4.74 (dd, J$_1$=8.5 Hz, J$_2$=2.0 Hz, 2H), 4.97 (d, J=8.0 Hz, 1H), 5.33 (d, J=8.0 Hz, 1H), 5.65 (d, J=7.2 Hz, 1H), 6.13 (s, 2H), 7.46 (d, J=7.2 Hz, 1H), 7.54 (t, J=8.0 Hz, 1H), 7.99 (s, 1H), 8.05 (d, J=8.0 Hz, 1H); $^{13}$C NMR (100 MHz, CDCl$_3$) δ 9.58, 15.19, 18.52, 21.83, 22.30, 25.79, 26.63, 28.32, 35.50, 35.74, 43.20, 51.72, 55.74, 58.66, 72.19, 72.47, 73.78, 75.78, 76.43, 77.39, 78.46, 79.26, 80.06, 81.10, 84.54, 119.53, 120.67, 121.58, 122.28, 130.46, 131.42, 132.49, 138.16, 143.79, 149.38, 155.56, 155.89, 165.55, 170.23, 204.05.

(b) 2-Debenzoyl-2-(3-trifluromethoxybenzoyl)-3'-dephenyl-10-propanoyl-3'-(2-methylpropyl)docetaxel (SB-T-111305)

White solid; $^1$H NMR (400 MHz, CDCl$_3$) δ 0.83-0.88 (m, 1H), 0.96-0.99 (m, 2H), 1.02-1.03 (m, 2H), 1.05 (s, 3H), 1.27 (s, 4H), 1.35 (s, 6H), 1.43 (s, 1H), 1.67 (s, 3H), 1.75 (d, J=11.6 Hz, 6H), 1.87 (dt, J=2.4 Hz, 11.6 Hz, 1H), 1.90 (s, 3H), 2.33 (s, 3H), 2.38 (t, J=8.8 Hz, 2H), 2.51-2.59 (m, 2H), 3.82 (d, J=7.2 Hz, 1H), 4.17 (t, J=8.8 Hz, 2H), 4.28 (d, J=8.4 Hz, 2H), 4.42 (dd, J=6.8 Hz, 1.2 Hz, 1H), 4.72 (s, 2H), 4.98 (d, J=8.2 Hz, 1H), 5.33 (d, J=5.6 Hz, 1H), 5.65 (d, J=7.2 Hz, 1H), 6.15 (t, J=9.2 Hz, 1H), 6.31 (s, 1H), 7.46 (d, J=8.0 Hz, 1H), 7.54 (t, J=8.0 Hz, 1H), 7.99 (s, 1H), 8.05 (d, J=8.0 Hz, 1H); $^{13}$C NMR (100 MHz, CDCl$_3$) δ 9.52, 13.23, 15.21, 18.60, 22.24, 25.87, 26.99, 28.40, 35.64, 43.37, 45.86, 51.80, 58.75, 72.53, 73.84, 75.73, 76.51, 79.41, 80.11, 81.23, 84.68, 120.74, 122.36, 126.36, 128.86, 130.52, 131.50, 132.95, 138.27, 143.12, 149.47, 155.59, 165.67, 170.21, 173.48, 175.34, 204.07

2-Debenzoyl-2-(3-trifluromethoxybenzoyl)-3'-dephenyl-10-(N,N-dimethylcarbamoyl)-3'-(2-methyl-2-propenyl)docetaxel (SB-T-121605)

White solid; $^1$H-NMR (400 MHz, CDCl$_3$, ppm) δ $^1$H-NMR (400 MHz, CDCl$_3$, ppm) δ 1.17 (s, 3H), 1.26 (s, 3H), 1.35 (s, 9H), 1.67 (s, 3H), 1.75 (s, 3H), 1.77 (s, 3H), 1.86-1.93 (m, 4H), 2.29-2.42 (m, 5H), 2.51-2.59 (m, 1H), 2.97 (s, 3H), 3.05 (s, 3H), 3.83 (d, J=7.0 Hz, 1H), 4.16-4.20 (m, 2H), 4.28 (d, J=8.2 Hz, 1H), 4.46 (dd, J=10.9 Hz, 6.3 Hz, 1H), 4.73-4.79 (m, 2H), 4.99 (d, J=8.2 Hz, 1H), 5.34 (d, J=6.3 Hz, 1H), 5.65 (d, J=7.0 Hz, 1H), 6.17 (t, J=8.0 Hz, 1H), 6.27 (s, 1H), 7.47 (d, J=8.0 Hz, 1H), 7.54 (t, J=8.0 Hz, 1H), 8.00 (s, 1H), 8.06 (d, J=8.0 Hz, 1H); $^{13}$C-NMR (100 MHz, CDCl$_3$, ppm) δ 9.51, 15.27, 18.60, 22.39, 25.87, 27.00, 28.41, 35.55, 35.66, 36.23, 36.86, 43.38, 45.80, 51.81, 58.71, 72.65, 72.70, 73.86, 75.96, 76.41, 76.51, 77.43, 79.52, 80.08, 81.29, 84.86, 120.75, 122.39, 126.34, 128.86, 130.51, 131.52, 133.23, 138.29, 143.41, 149.46, 155.59, 156.33, 165.69, 170.16, 173.47, 205.87; $^{19}$F NMR (376 MHz, CDCl$_3$) δ −57.82 (s, 3F); HRMS (TOF) m/z: Calcd. For $C_{45}H_{59}F_3N_2O_{16}H^+$, 941.3889. Found, 941.3893.

2-Debenzoyl-2-(3-trifluromethoxybenzoyl)-3'-dephenyl-10-(methoxycarbonyl)-3'-(2-methyl-2-propenyl)docetaxel (SB-T-121705)

White solid; $^1$H NMR (500 MHz, CDCl$_3$) δ 1.15 (s, 3H), 1.24 (t, J=4.0 Hz, 4H), 1.33 (s, 9H), 1.68 (s, 4H), 1.72 (s, 4H), 1.75 (s, 3H), 1.87 (dt, J$_1$=3.0 Hz, J$_2$=9.5 Hz, 1H), 1.93 (s, 3H), 2.03 (s, 1H), 2.33 (s, 4H), 2.38-2.43 (m, 1H), 2.49 (d, J=4.5 Hz, 1H), 2.53-2.59 (m, 1H), 3.37 (d, J=6.5 Hz, 1H), 3.79 (d, J=7.0 Hz, 1H), 3.86 (s, 3H), 4.09 (dd, J=8.5 Hz, 7.0 Hz, 1H), 4.17 (t, J=2.5 Hz, 2H), 4.27 (d, J=3.0 Hz, 1H), 4.40 (dt, J=4.5 Hz, 2.0 Hz, 1H), 4.74 (dd, J=8.5 Hz, 2.0 Hz, 2H), 4.97 (d, J=8.0 Hz, 1H), 5.33 (d, J=8.0 Hz, 1H), 5.65 (d, J=7.0 Hz, 1H), 6.13 (s, 2H), 7.46 (d, J=8.0 Hz, 1H), 7.54 (t, J=8.0 Hz, 1H), 7.99 (s, 1H), 8.05 (d, J=8.0 Hz, 1H); $^{13}$C NMR NMR (400 MHz, CDCl$_3$) δ 9.58, 15.19, 18.52, 21.83, 22.30, 25.79, 26.63, 28.32, 35.50, 35.74, 43.20, 51.72, 55.74, 58.66, 72.19, 72.47, 73.78, 75.78, 76.43, 77.39, 78.46, 79.26, 80.06, 81.10, 84.54, 119.53, 120.67, 121.58, 122.28, 130.46, 131.42, 132.49, 138.16, 143.79, 149.38, 155.56, 155.89, 165.55, 170.23, 204.05.

(c) 2-Debenzoyl-2-(3-trifluromethoxybenzoyl)-3'-dephenyl-10-(methoxycarbonyl)-3'-(2-methylpropyl)docetaxel (SB-T-111705)

White solid; $^1$H NMR (500 MHz, CDCl$_3$) δ 1.14 (s, 3H), 1.23 (t, J=6.0 Hz, 8H), 1.30 (s, 10H), 1.66 (d, J=10 Hz, 5H), 1.74 (d, J=11.2 Hz, 6H), 1.90 (s, 4H), 2.33 (s, 5H), 2.54 (m, 4H), 3.34 (s, 1H), 3.82 (d, J=5.6 Hz, 1H), 4.17 (m, 2H), 4.27 (d, J=6.8 Hz, 1H), 4.42 (s, 1H), 4.72 (dd, J=7.6 Hz, 6.8 Hz, 2H), 4.97 (d, J=6.4 Hz, 1H), 5.65 (d, J=5.6 Hz, 1H), 5.65 (d, J=5.6 Hz, 1H), 6.14 (t, J=6.4 Hz, 1H), 6.32 (s, 1H), 7.45 (d, J=7.8 Hz, 1 Hz), 7.53 (t, J=7.8 Hz, 1H), 7.98 (s, 1H), 8.04 (d, J=7.8 Hz, 1H); $^{13}$C NMR (125 MHz, CDCl$_3$) δ 9.22, 9.68, 15.16, 18.58, 21.99, 22.37, 25.85, 27.76, 28.38, 35.60, 35.73, 43.36, 45.85, 58.73, 72.39, 72.61, 73.82, 75.62, 75.80, 76.50, 79.34, 80.11, 81.21, 84.63, 120.69, 122.34, 126.35, 128.84, 130.51, 131.48, 132.94, 149.43, 155.59, 165.63, 170.22, 174.83, 203.95.

2-Debenzoyl-2-(3-trifluromethoxybenzoyl)-10-methyl-3'-dephenyl-3'-(2-methyl-2-propenyl)-docetaxel (SB-T-123005)

White solid; $^1$H-NMR (400 MHz, CDCl$_3$) δ $^1$H-NMR (400 MHz, CDCl$_3$, ppm) δ 1.20 (s, 3H), 1.22 (s, 3H), 1.36 (s, 9H), 1.69 (s, 3H), 1.75 (s, 3H), 1.77 (s, 3H), 1.79-1.85 (m, 1H), 1.95 (s, 3H), 2.29-2.44 (m, 5H), 2.56-2.63 (m, 3H), 3.45 (s, 3H), 3.90 (d, J=7.0 Hz, 1H), 4.16-4.30 (m, 4H), 4.73-4.80 (m, 2H), 4.96-4.99 (m, 2H), 5.34 (d, J=8.0 Hz, 1H), 5.67 (d, J=7.0 Hz, 1H), 6.17 (d, J=8.7 Hz, 1H), 7.47 (d, J=8.0 Hz, 1H), 7.54 (t, J=8.0 Hz, 1H), 7.99 (s, 1H), 8.05 (d, J=8.0 Hz, 1H); $^{13}$C-NMR (100 MHz, CDCl$_3$, ppm) δ 9.89, 14.82, 18.62, 20.97, 22.40, 25.88, 26.47, 28.42, 35.50, 37.23, 43.36, 46.98, 51.78, 56.96, 58.06, 72.13, 72.60, 73.86, 75.67, 76.66, 77.43, 79.11, 80.09, 81.39, 82.88, 84.47, 119.34, 120.80, 122.37, 126.33, 128.86, 130.50, 131.56, 134.89, 138.21, 140.02, 149.44, 155.56, 165.67, 170.30, 173.40, 206.89; $^{19}$F NMR (376 MHz, CDCl$_3$) δ −57.82 (s, 3F); HRMS (TOF) m/z: Calcd. For $C_{43}H_{56}F_3NO_{15}Na^+$ 906.3494. Found, 906.3500.

2-Debenzoyl-2-(3-trifluromethoxybenzoyl)-7,10-dimethyl-3'-dephenyl-3'-(2-methyl-2-propenyl)-docetaxel (SB-T-1230105)

White solid; $^1$H-NMR (400 MHz, CDCl$_3$, ppm) δ 1.22 (s, 6H), 1.37 (s, 9H), 1.72 (s, 3H), 1.75-1.84 (m, 7H), 1.97 (s, 3H), 2.24-2.30 (m, 1H), 2.33 (s, 3H), 2.38-2.45 (m, 1H), 2.68-2.76 (m, 1H), 3.31 (s, 3H), 3.46 (s, 3H), 3.84-3.90 (m, 2H), 4.16 (d, J=8.28 Hz, 1H), 4.21-4.22 (m, 1H), 4.29 (d, J=8.2 Hz, 1H), 4.74-4.80 (m, 2H), 4.83 (s, 1H), 5.01 (d, J=8.2 Hz, 1H), 5.33 (d, J=7.8 Hz, 1H), 5.62 (d, J=7.0 Hz, 1H), 6.16 (d, J=8.6 Hz, 1H), 7.46 (d, J=8.0 Hz, 1H), 7.54 (t, J=8.0 Hz, 1H), 7.98 (s, 1H), 8.05 (d, J=8.0 Hz, 1H); $^{13}$C-NMR (100 MHz, CDCl$_3$, ppm) δ 10.50, 14.96, 18.64, 20.81, 22.47, 25.90, 26.85, 28.43, 32.30, 35.33, 43.47, 47.61, 51.74, 57.08, 57.26, 57.51, 72.66, 73.85, 75.40, 76.58, 77.43, 79.07, 80.09, 80.91, 81.84, 82.87, 84.32, 119.35, 120.76, 121.91, 122.34, 126.31, 128.86, 130.47, 131.57, 135.49, 138.30, 139.41, 149.44, 155.52, 165.61, 170.44, 173.26, 205.11; $^{19}$F NMR (376 MHz, CDCl$_3$) δ −57.82 (s, 3F); HRMS (TOF) m/z: Calcd. For $C_{44}H_{58}F_3NO_{15}Na^+$ 920.3651. Found, 920.3649.

(d) 2-Debenzoyl-2-(3-difluromethoxybenzoyl)-3'-dephenyl-10-acetyl-3'-(2-methyl-2-propenyl)docetaxel (SB-T-121206)

White solid; $^1$H NMR (500 MHz, CDCl$_3$) δ 1.15 (s, 3H), 1.29-1.22 (m, 4H), 1.32 (s, 7H), 1.58 (d, J=14.2 Hz, 3H), 1.68 (s, 3H), 1.75 (dd, J=12.6, 1.1 Hz, 5H), 1.95-1.86 (m, 3H), 2.04 (s, 1H), 2.24 (s, 3H), 2.40-2.28 (m, 4H), 2.47 (d, J=4.2 Hz, 1H), 2.56 (ddd, J=14.8, 9.6, 6.8 Hz, 1H), 3.30 (d, J=5.5 Hz, 1H), 3.82 (d, J=6.8 Hz, 1H), 4.12 (q, J=7.1 Hz, 1H), 4.17 (d, J=8.2 Hz, 1H), 4.20 (d, J=6.8, 2.2 Hz, 1H), 4.31 (d, J=8.2 Hz, 1H), 4.43 (ddd, J=10.9, 6.8, 4.2 Hz, 1H), 4.74 (t, J=5.8 Hz, 2H), 4.98 (d, J=7.7 Hz, 1H), 5.34 (s, 1H), 5.66 (d, J=7.1 Hz, 1H), 6.18 (dd, J=9.1, 7.7 Hz, 1H), 6.30 (s, 1H), 6.67 (t, J=73.3 Hz, 2H), 7.37 (dd, J=7.7, 2.2 Hz, 1H), 7.56-7.45 (m, 1H), 7.89 (s, 1H), 8.00-7.92 (m, 1H).

(e) 2-Debenzoyl-2-(3-difluromethoxybenzoyl)-3'-dephenyl-10-propanoyl-3'-(2-methyl-2-propenyl)docetaxel (SB-T-121306)

White solid: $^1$H-NMR (400 MHz, CDCl$_3$, ppm) δ 1.15 (s, 3H), 1.21-1.26 (m, 6H), 1.33 (s, 9H), 1.68 (s, 3H), 1.75 (s, 3H), 1.77 (s, 3H), 1.85-1.92 (m, 4H), 2.30-2.38 (m, 5H), 2.47-2.60 (m, 3H), 3.83 (d, J=7.0 Hz, 1H), 4.17 (d, J=8.3 Hz, 1H), 4.21 (d, J=2.3 Hz, 1H), 4.31 (d, J=8.3 Hz, 1H), 4.44 (dd, J=10.8 Hz, 6.7 Hz, 1H), 4.75-4.81 (m, 2H), 4.98 (d, J=7.8 Hz, 1H), 5.34 (d, J=7.8 Hz, 1H), 5.66 (d, J=7.1 Hz, 1H), 6.18 (t, J=8.5 Hz, 1H), 6.67 (d, J=73.4 Hz, 1H), 7.36-7.38 (m, 1H), 7.49 (t, J=8.0 Hz, 1H), 7.89 (s, 1H), 7.96 (d, J=8.0 Hz, 1H); $^{13}$C-NMR (100 MHz, CDCl$_3$, ppm) δ 9.23, 9.72, 15.12, 18.67, 22.08, 22.48, 25.89, 26.83, 27.77, 28.39, 35.63, 35.73, 43.37, 45.83, 51.66, 58.72, 72.37, 72.54, 73.83, 75.61, 75.76, 76.53, 77.43, 79.42, 80.07, 81.18, 84.65, 113.29, 115.88, 118.48, 120.36, 120.77, 125.11, 127.41, 130.45, 131.28, 133.01, 138.17, 142.84, 151.42, 155.59, 166.03, 170.33, 173.48, 174.82, 203.98; $^{19}$F NMR (376 MHz, CDCl$_3$) δ −81.13 (ABq, J=167 Hz) (2F); HRMS (TOF) m/z: Calcd. For $C_{45}H_{59}F_2NO_{16}H^+$, 908.3875. Found, 908.3882.

(f) 2-Debenzoyl-2-(3-difluromethoxybenzoyl)-3'-dephenyl-10-cyclopropanecarbonyl-3'-(2-methyl-2-propenyl)docetaxel (SB-T-121406)

White solid: $^1$H-NMR (400 MHz, CDCl$_3$, ppm) δ 0.98-1.02 (m, 2H), 1.11-1.15 (m, 4H), 1.26 (s, 3H), 1.32 (s, 9H), 1.66 (s, 3H), 1.74 (s, 3H), 1.76 (s, 3H), 1.78-1.82 (m, 1H), 1.86-1.89 (m, 4H), 2.30-2.38 (m, 5H), 2.50-2.58 (m, 2H), 3.81 (d, J=7.0 Hz, 1H), 4.16 (d, J=8.3 Hz, 1H), 4.20 (d, J=2.6 Hz, 1H), 4.29 (d, J=8.3 Hz, 1H), 4.39-4.43 (m, 1H), 4.72-4.77 (m, 1H), 4.83 (d, J=8.7 Hz, 1H), 4.97 (d, J=8.0 Hz, 1H), 5.33 (d, J=8.4 Hz, 1H), 5.65 (d, J=7.1 Hz, 1H), 6.17 (t, J=9.0 Hz, 1H), 6.66 (t, J=73.4 Hz, 1H), 7.35-7.37 (m, 1H), 7.48 (t, J=8.0 Hz, 1H), 7.87 (s, 1H), 7.95 (d, J=8.0 Hz, 1H); $^{13}$C-NMR (100 MHz, CDCl$_3$, ppm) δ 9.20, 9.43, 9.50, 13.04, 14.93, 18.46, 21.97, 22.27, 25.69, 26.68, 28.19, 35.46, 35.49, 43.17, 45.64, 51.45, 58.49, 72.14, 72.34, 73.63, 75.40, 75.60, 76.33, 77.25, 79.18, 79.87, 80.99, 84.47, 113.10, 115.69, 118.29, 120.15, 120.59, 124.88, 127.20, 130.24, 131.10, 132.83, 137.92, 142.74, 151.21, 155.41, 165.81, 170.13, 173.27, 175.12, 203.86; $^{19}$F NMR (376 MHz, CDCl$_3$) δ −81.24 (ABq, J=167 Hz) (2F); HRMS (TOF) m/z: Calcd. For $C_{46}H_{59}F_2NO_{16}Na^+$, 942.3694. Found, 942.3694.

(g) 2-Debenzoyl-2-(3-difluromethoxybenzoyl)-3'-dephenyl-10-(N,N-dimethylcarbamoyl-3'-(2-methyl-2-propenyl)docetaxel (SB-T-121606)

White solid: $^1$H-NMR (400 MHz, CDCl$_3$, ppm) δ $^1$H-NMR (400 MHz, CDCl$_3$, ppm) δ 1.16 (s, 3H), 1.26 (s, 3H), 1.33 (s, 9H), 1.67 (s, 3H), 1.75 (s, 3H), 1.77 (s, 3H), 1.85-1.92 (m, 4H), 2.30-2.41 (m, 5H), 2.50-2.58 (m, 1H), 2.96 (s, 3H), 3.05 (s, 3H), 3.82 (d, J=7.0 Hz, 1H), 4.16-4.21 (m, 2H), 4.30 (d, J=8.3 Hz, 1H), 4.46 (dd, J=10.9 Hz, 6.6 Hz, 1H), 4.75-4.82 (m, 2H), 4.99 (d, J=7.9 Hz, 1H), 5.33 (d, J=8.1 Hz, 1H), 5.65 (d, J=7.1 Hz, 1H), 6.19 (t, J=8.1 Hz, 1H), 6.67 (t, J=73.4 Hz, 1H), 7.35-7.38 (m, 1H), 7.49 (t, J=7.9 Hz, 1H), 7.88 (s, 1H), 7.96 (d, J=7.9 Hz, 1H); $^{13}$C-NMR (100 MHz, CDCl$_3$, ppm) δ 9.54, 15.19, 18.67, 22.48, 25.89, 27.02, 28.39, 35.55, 35.68, 36.23, 36.85, 43.37, 45.77, 51.65, 58.66, 72.62, 73.84, 75.89, 76.39, 76.52, 77.43, 79.51, 80.05, 81.24, 84.86, 113.30, 115.89, 118.48, 120.36, 120.78, 125.08, 127.40, 130.43, 131.31, 133.30, 138.16, 143.26, 151.42, 155.60, 156.33, 166.04, 170.27, 173.48, 205.86; $^{19}$F NMR (376 MHz, CDCl$_3$) δ −81.23 (ABq, J=167 Hz) (2F); HRMS (TOF) m/z: Calcd. For $C_{45}H_{60}F_2N_2O_{16}Na^+$, 945.3803. Found, 945.3794.

(h) 2-Debenzoyl-2-(3-difluromethoxybenzoyl)-3'-dephenyl-10-(methoxycarbonyl-3'-(2-methyl-2-propenyl)docetaxel (SB-T-121706)

White solid: $^1$H-NMR (400 MHz, CDCl$_3$, ppm) δ $^1$H-NMR (400 MHz, CDCl$_3$, ppm) δ 1.16 (s, 3H), 1.26 (s, 3H), 1.33 (s, 9H), 1.70 (s, 3H), 1.75 (s, 3H), 1.77 (s, 3H), 1.86-1.94 (m, 4H), 2.30-2.42 (m, 5H), 2.53-2.61 (m, 1H), 3.81 (d, J=7.04 Hz, 1H), 3.88 (s, 3H), 4.17-4.21 (m, 2H), 4.32 (d, J=8.4 Hz, 1H), 4.46 (dd, J=10.8 Hz, 6.6 Hz, 1H), 4.73-4.79 (m, 2H), 4.98 (d, J=8.2 Hz, 1H), 5.34 (d, J=7.1 Hz, 1H), 5.66 (d, J=7.0 Hz, 1H), 6.13 (s, 1H), 6.18 (t, J=8.8 Hz, 1H), 6.67 (t, J=73.4 Hz, 1H), 7.36-7.38 (m, 1H), 7.50 (t, J=8.0 Hz, 1H), 7.89 (s, 1H), 7.96 (d, J=8.0 Hz, 1H); $^{13}$C-NMR (100 MHz, CDCl$_3$, ppm) δ 9.67, 15.23, 18.68, 21.99, 22.48, 25.90, 26.76, 28.40, 35.57, 35.78, 43.27, 45.79, 51.67, 55.81, 58.75, 72.27, 72.48, 73.84, 75.69, 76.53, 77.49, 78.49, 79.43, 80.11, 81.14, 84.60, 113.30, 115.89, 118.48, 120.34, 120.75, 125.13, 127.42, 130.46, 131.26, 132.60, 138.20, 143.85, 151.43, 155.61, 155.98, 166.03, 170.38, 173.54, 204.16; $^{19}$F NMR (376 MHz, CDCl$_3$) δ −81.24 (ABq, J=167 Hz) (2F); HRMS (TOF) m/z: Calcd. For $C_{44}H_{57}F_2NO_{17}H^+$, 910.3667. Found, 910.3671.

(i) 2-Debenzoyl-2-(3-difluromethoxybenzoyl)-7,10-dimethyl-3'-dephenyl-3'-(2-methyl-2-propenyl)-docetaxel (SB-T-1230106)

White solid: $^1$H-NMR (400 MHz, CDCl$_3$, ppm) δ 1.20 (s, 3H), 1.21 (s, 3H), 1.35 (s, 9H), 1.71 (s, 3H), 1.73 (s, 3H), 1.75-1.83 (m, 4H), 1.96 (s, 3H), 2.25-2.41 (m, 5H), 2.67-2.75 (m, 1H), 3.31 (s, 3H), 3.45 (s, 3H), 3.83-3.90 (m, 2H), 4.16 (d, J=8.2 Hz, 1H), 4.22 (d, J=2.6 Hz, 1H), 4.30 (d, J=8.24 Hz, 1H), 4.76-4.83 (m, 3H), 5.00 (d, J=8.2 Hz, 1H), 5.33 (d, J=8.3 Hz, 1H), 5.61 (d, J=7.0 Hz, 1H), 6.18 (t, J=8.2 Hz, 1H), 6.64 (t, J=73.4 Hz, 1H), 7.35-7.37 (m, 1H), 7.49 (t, J=8.0 Hz, 1H), 7.88 (s, 1H), 7.95 (d, J=8.0 Hz, 1H); $^{13}$C-NMR (100 MHz, CDCl$_3$, ppm) δ 10.52, 14.91, 18.70, 20.89, 22.56, 25.92, 26.88, 28.42, 32.27, 35.35, 43.46, 47.56, 51.63, 57.06, 57.26, 57.50, 72.61, 73.84, 75.34, 76.60, 77.43, 79.07, 80.06, 80.90, 81.79, 82.84, 84.32, 113.29, 115.89, 118.48, 120.49, 120.79, 125.08, 127.43, 130.40, 131.37, 135.53, 138.20, 139.35, 151.35, 155.53, 165.97, 170.54, 173.29, 205.14; $^{19}$F NMR (376 MHz, CDCl$_3$) δ −81.12 (ABq, J=167 Hz) (2F); HRMS (TOF) m/z: Calcd. For $C_{44}H_{59}F_2NO_{15}H^+$, 880.3926. Found, 880.3931.

We claim:

1. A taxoid compound represented by the formula:

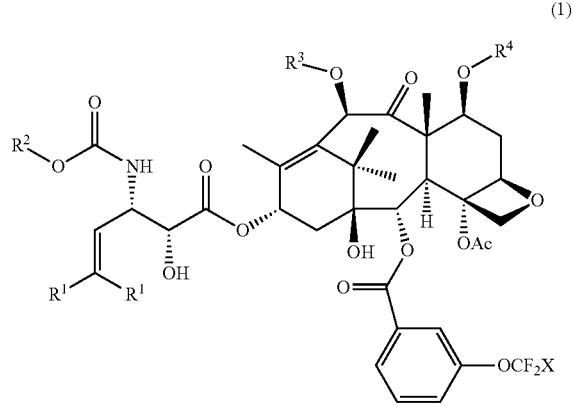

(1)

wherein:
$R^1$ represents a methyl group or a fluorine;
$R^2$ represents an alkyl or alkenyl group having one to six carbon atoms; or a cycloalkyl or cycloalkenyl group having three to seven ring carbon atoms;
$R^3$ represents an alkyl, alkenyl, dialkylamino, alkylamino, or alkoxy group having one to six carbon atoms; a cycloalkyl or cycloalkenyl group having three to seven ring carbon atoms; an aryl group having six to eighteen ring carbon atoms; acetyl, propanoyl, cyclopropanecarbonyl, N,N-dimethylcarbamoyl, or methoxycarbonyl;

$R^4$ represents hydrogen or a methyl group; and

X represents hydrogen or fluorine.

2. The taxoid compound according to claim 1, wherein $R^2$ represents tert-butyl.

3. The taxoid compound according to claim 1, wherein $R^1$ represents methyl, $R^2$ represents tert-butyl.

4. The taxoid compound according to claim 1, wherein $R^1$ represents fluorine, $R^2$ represents tert-butyl.

5. The taxoid compound according to claim 1, wherein $R^1$ represents methyl, $R^2$ represents tert-butyl, and X represents fluorine.

6. The taxoid compound according to claim 1, wherein $R^1$ represents fluorine, $R^2$ represents tert-butyl, and X represents fluorine.

7. The taxoid compound according to claim 1, wherein $R^1$ represents methyl, $R^2$ represents tert-butyl, and X represents hydrogen.

8. The taxoid compound according to claim 1, wherein $R^1$ represents fluorine, $R^2$ represents tert-butyl, and X represents hydrogen.

9. A pharmaceutical composition comprising a taxoid compound according to claim 1 and a pharmaceutically acceptable carrier.

10. A method for inhibiting the growth of cancer cells in a mammal in need thereof, the method comprising administering to the mammal an effective amount of a taxoid compound according to claim 1, wherein the cancer is breast, ovarian, colon or pancreatic cancer.

* * * * *